United States Patent [19]

Rabinowitz

[11] Patent Number: 4,688,569
[45] Date of Patent: Aug. 25, 1987

[54] FINGER ACTUATED SURGICAL ELECTRODE HOLDER

[75] Inventor: Dan Rabinowitz, Chicago, Ill.

[73] Assignee: Medi-Tech, Inc., Chicago, Ill.

[21] Appl. No.: 872,166

[22] Filed: Jun. 9, 1986

[51] Int. Cl.<sup>4</sup> ............................................. A61B 17/36
[52] U.S. Cl. ............................ 128/303.14; 128/303.17
[58] Field of Search ........................................ 128/4–8, 128/23, 303.1, 303.13–303.17

[56] References Cited

U.S. PATENT DOCUMENTS

| | | | |
|---|---|---|---|
| 1,038,011 | 9/1912 | Snell | 128/23 |
| 1,945,327 | 1/1934 | Morse | 128/303.17 |
| 3,295,514 | 1/1967 | Hein et al. | 128/303.17 |
| 3,906,955 | 9/1975 | Roberts | 128/303.17 |
| 4,325,374 | 4/1982 | Komiya | 128/303.15 |
| 4,545,375 | 10/1985 | Cline | 128/303.17 |

FOREIGN PATENT DOCUMENTS

| | | | |
|---|---|---|---|
| 179607 | 2/1954 | Fed. Rep. of Germany | 128/303.17 |
| 515956 | 12/1939 | United Kingdom | 128/303.17 |

*Primary Examiner*—Kyle L. Howell
*Assistant Examiner*—Max F. Hindenburg

[57] ABSTRACT

A hand held holder, incorporating a light transmitting electrode tip that's separable from the handle, for use in high frequency electrosurgery, with built-in, finger actuated switches for operating a high frequency current generator. The device is particularly characterized in that in conjunction with a light transmitting electrode, it provides localized illumination at the region of surgery. To provide this illumination, an elongate photoconductive device is provided which extends generally longitudinally within the electrode, and communicates in the holder with a light transmitting portion, in the form of either a section of a strand like photoconductor, or an electrically operated lamp.

12 Claims, 10 Drawing Figures

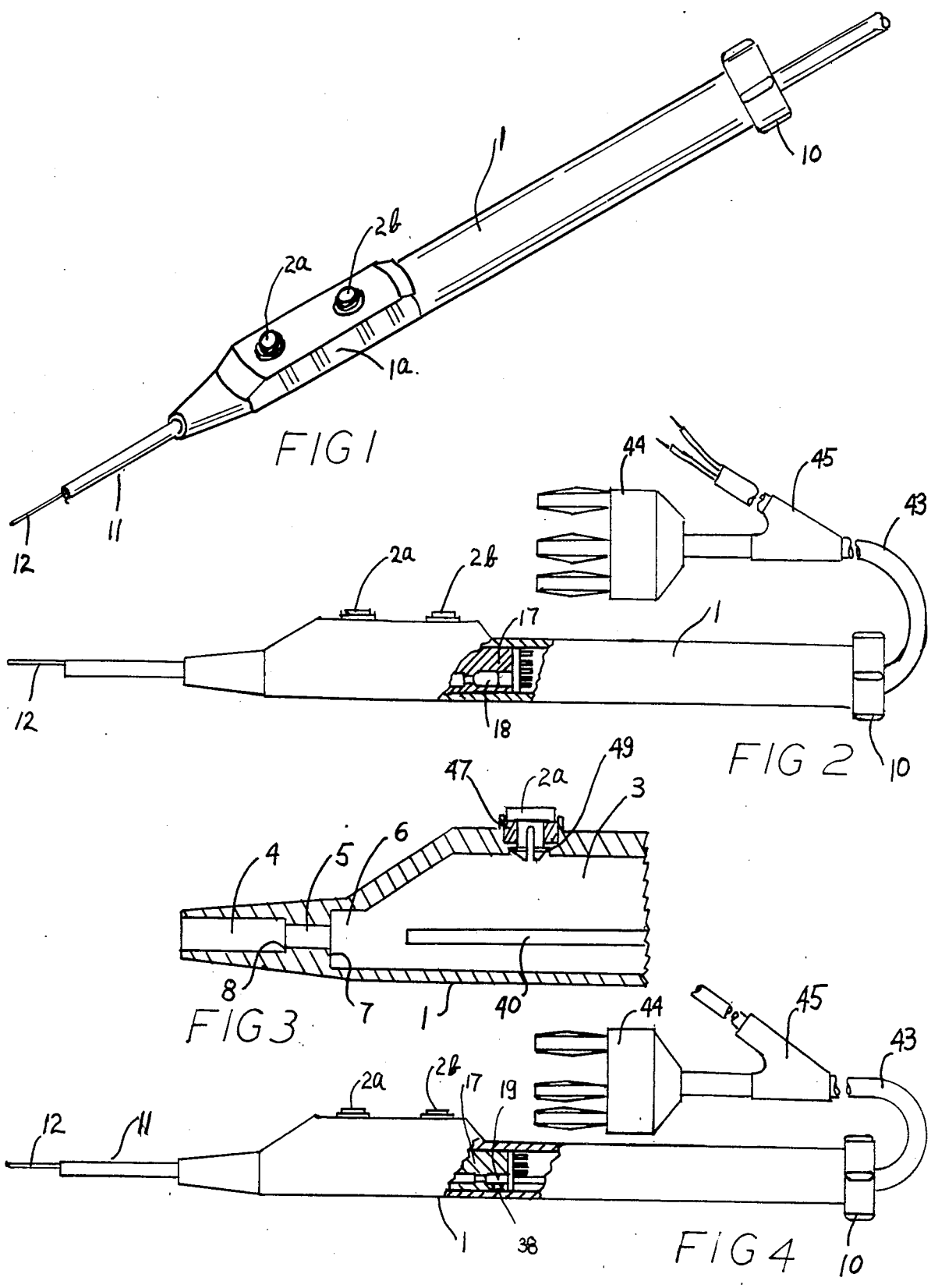

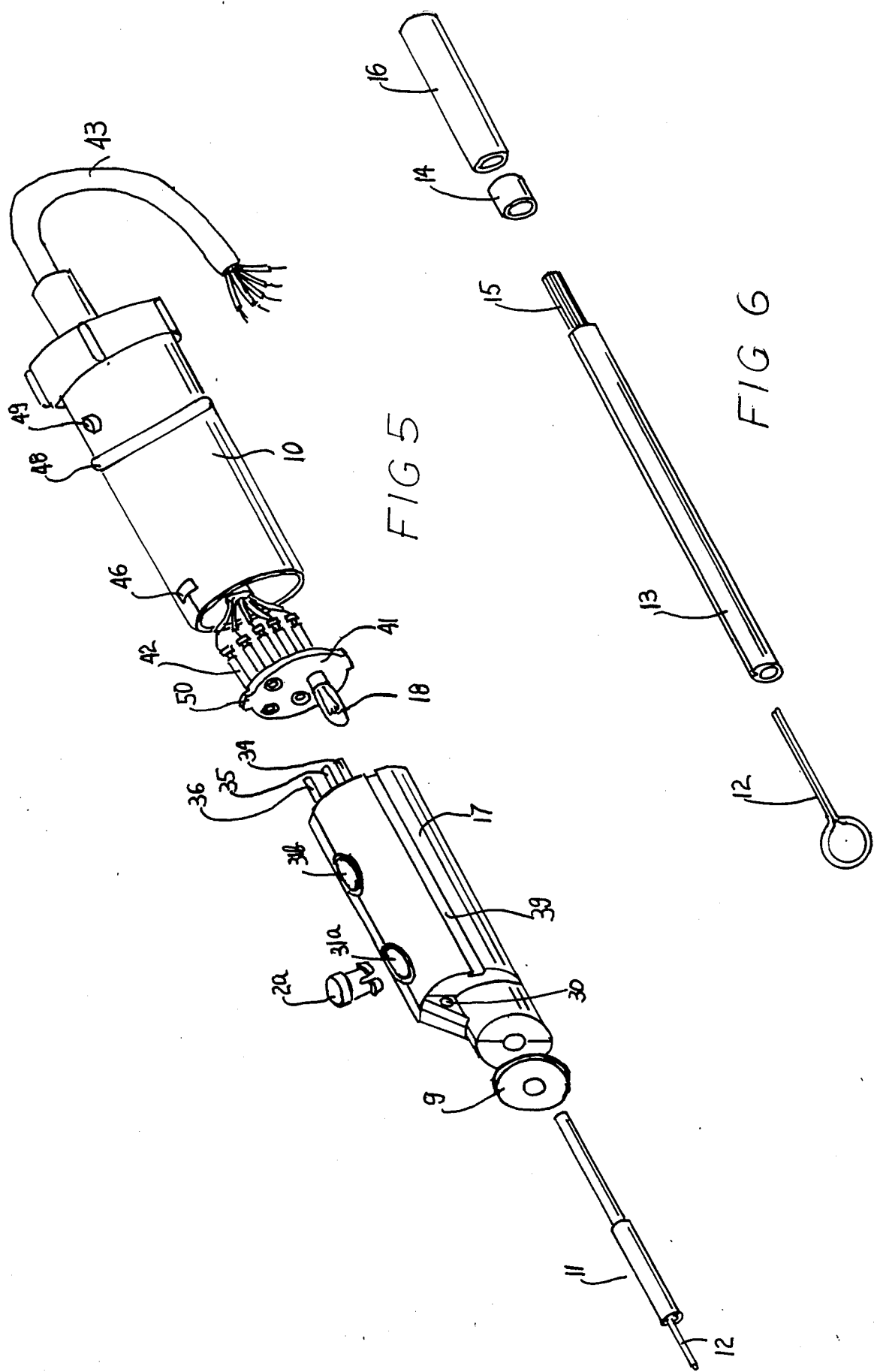

FINGER ACTUATED SURGICAL ELECTRODE HOLDER

BACKGROUND

Electrosurgery is a form of surgery in which living body tissue is removed or destroyed by heat generated by a high frequency current. A variety of systems for supplying the current have been developed. Most of them utilize an active and an indifferent electrode. The indifferent electrode is often a large metal plate which is placed on the leg, arm, or back of the patient.

The high frequency current radiates through the tissues from the site of tissue contact of the small active electrode toward the larger indifferent electrode, than back to a power oscillator of an electrosurgical unit, and back again to the site of tissue contact of the small electrode, in a continuing radiating cycle. In this manner, the current is not evenly dispersed but instead attains a density or concentration at the site of the small electrode tissue contact that is great enough to produce cellular destruction, known as electrosurgery.

The active electrode may have a wide variety of shapes such as a needle for cutting, or a wire loop for scraping.

When touched by the active electrode, tissue is disintegrated, but the heat generated does not penetrate the body deeply. Thus, the active electrode acts as a scalpel with the advantage that in the process of cutting, small blood vessels are sealed by the heat thereby reducing bleeding.

A number of electrosurgical instruments have been developed and used whereby an active electrode is attached to an insulated handle and a high frequency current is applied thereto. Electrosurgical instruments found to be particularly safe and effective for surgical applications are those which incorporate finger actuated switches, those which allow for readily interchangeable electrodes, those which are water resistant, and those which are thin and properly balanced for close surgical use where a certain "feel" is necessary for the surgeon to properly use the instrument. An instrument such as the aforedescribed one is commonly referred to as an "electrosurgical pencil", particularly in view of its slenderness, and shape which resembles a pencil.

The incorporation of light sources into electrosurgery handles to illuminate the localized area in which the doctor or surgeon intends to cut or coagulate is highly desirable. Conventionally, light is directed to the work area by means of overhead lamps. The shadows which result from such lighting, and the general inefficiency of such an arrangement is apparent to those skilled in the art, particularly when surgery needs to be performed in hard to reach areas such as the throat, nose and ears.

Illumination of surgical instruments is not new as for example disclosed in U.S. Pat. No. 2,029,487 or U.S. Pat. No. 1,038,011. However, the effective incorporation of illumination into modern day electrosurgical handles that provide finger actuated switching within handles that are very inexpensive, slim and waterproof, and which can accommodate and hold a readily insertable and releasable electrode, is nonexistent.

This invention relates to the effective incorporation of illumination into such an electrosurgical handle.

One object of the invention is to provide a simple and inexpensive means for incorporating light sources into electrosurgical pencils that have finger actuated switches, that do not allow seepage of contaminants at the end of the handle where the electrode is inserted and that maintain the slenderness, shape and balance required or preferred by surgeons for good visibility and effective function.

Another object of the invention is to provide a light transmitting electrode that can be removably attached to an electrosurgical generator interfacing handle.

Another object of the invention is to provide an electrosurgical pencil with light with easy means for replacement of its light source.

Another object of the invention is to provide an electrosurgical pencil that is useable with either a light transmitting or non-light transmitting, i.e., standard, electrode.

Another object of the invention is to provide an electrosurgical pencil that can accommodate either a lamp light source or a Fiber Optic bundle, each of which transmit light to the light transmitting electrode.

A further object of the invention is to provide a novel way of assembling the pencil so that the switch body is properly aligned with the finger actuated switch buttons.

A further object of the present invention is to provide an electrosurgical handle incorporating a light source which can be manufactured in a simple and economical manner, thereby, permitting the same to be discarded after a single use.

A further object of the invention is to provide an electrode that incorporates a light transmitting element that provides light adjacent to the surgically functioning portion or wire of the electrode.

A further object of the invention is to provide a handle which permits the electrode to be readily inserted and releasably held in position, with a spring element that also acts as an electrical contacting member.

A further object of the invention is to provide a handle for electrosurgery which incorporates a finger actuated, snap action switch and also a chamber for a light source.

A further object of the invention is to provide an inexpensive, safe and effective method for fabricating the light transmitting electrode.

The foregoing and other objects, features and advantages will be more apparent in view of the following detailed description of exemplary preferred embodiments, when taken in conjunction with the accompanying drawings.

DRAWINGS

FIG. 1 is a perspective view of the electrosurgical handle holding an electrode in place.

FIG. 2 is a side view, partially in section, of the electrosurge handle incorporating an incandescent lamp as a light source.

FIG. 3 is a fragmentary detail, enlarged and in section, of the electrode end of the handle when it does not include internal components.

FIG. 4 is a side view, partly in section, similar to FIG. 2, but showing a Fiber Optic bundle as the member that transmits light to the electrosurgical electrode.

FIG. 5 is an exploded view of the elements that go into the electrosurgical handle.

FIG. 6 is an exploded view of an electrode.

DESCRIPTION OF THE PREFERRED EMBODIMENTS

Figure 7:
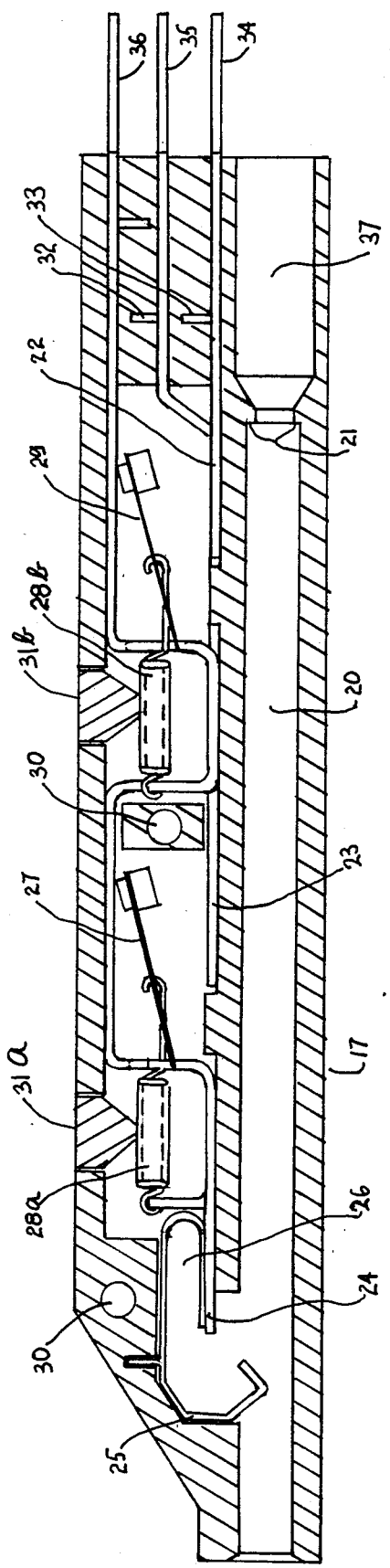
FIG. 7 is an enlarged sectional view of the switch assembly.

Referring now to the drawings, handle 1, as shown in FIGS. 1, 2, 3, and 4, is a substantially rigid elongated hollow tube. It is shown with a flat sided portion 1a, which permits it to be firmly gripped by the operating surgeon. Buttons 2a and 2b are used to finger activate a switch within the handle. Main bore 3 in handle 1, as shown in FIG. 3, extends from the connecting end (at the right in the drawing) to a point adjacent to the electrode end at which end are formed smaller bores 4, 5, and 6. Bore 5 is smaller than bore 4 and bore 6, and provides a neck between them forming shoulder 7 facing inward and shoulder 8 facing outward toward the electrode tip.

End cap 10 closes the connecting end of handle 1. Handle 1 and end cap 10 are both made of a suitable electrical insulating, sterilizable, rigid and substantially unbreakable plastic of a type well known in the art.

Turning specifically to FIGS. 5 and 6, the mechanical elements within the handle and end cap will now be described in detail. Electrode 11 is comprised of a thin wire 12, usually of tungsten material, that is of varying shapes and that is kept in electrical contact with a hollow tubular metallic element 13, that's filled with glass fibers 15 or other photoconductive elements. The ends of the glass fibers are usually glued together with epoxy and polished. The wire may be kept secure, and in effective electrical contact with the tubular element 13 by soldering and mechanical means including a tight fitting or shrink fitting electrically insulating sleeve 16 that is telescoped over the tubular element 13. Another alternate means of securing the wire in place is by means of a securing collar 14 that is telescoped over the tube 13 and over the wire that is in contact with the tube. The collar, in turn, may be crimped in place. The assembly of tube, wire, and securing collar can then be insulated by a tight fitting or shrink fitting insulating sleeve 16. Once insulated, the collar can provide a mechanical grip for the surgeon to more easily remove the electrode from the holder. As such, it serves as both a securing collar and a gripping element.

For enhanced electrical, surgical, and sterilizable properties, the tubular element 13 will preferrably be made of stainless steel. Electrically insulating sleeve 16 will preferrably be made of a sterilizable plastic and is substantially shorter than tubular element 13.

Bushing 9 fits within bore 6 and is seated against shoulder 7 therein. This bushing is preferrably made of a flexible, sterilizable compound such as silicone rubber. A hole in the center of the bushing is meant to mate with the tubular element 13 of the electrode, and is slightly smaller in diameter than the outer diameter of the tubular element 13, thereby providing a tight seal around the electrode.

Switch housing 17, as shown in FIGS. 2, 4, 5, and in more detail in FIG. 7, is used to accommodate lamp 18 or a light transmitting bundle 19 of Fiber Optic photoconductive elements that is colinear with the electrode 11 when attached to the handle. Switch housing 17 also incorporates a channel 20 that accommodates the electrode. At the end of the channel 20 is a shoulder 21 upon which the electrode seats when pushed as far as it can go in the said channel, at which point it is a predetermined and optimum distance from lamp 18.

The switch housing also accommodates electrical conductors 22, 23 and 24. Conductor 24 is a common conductor, whereas conductor 22 completes a circuit carrying coagulating current, and conductor 23 completes a circuit carrying cutting current.

Spring element 25 makes electrical contact with common conductor 24 by a wedging action that occurs as the spring element is assembled into pocket 26 in the switch housing, along with conductor 24.

The switch housing also incorporates a contact leaf 27 that snaps by an over-toggle action into electrical contact with conductor 23 when spring 28a is depressed. Likewise, contact leaf 29 snaps into electrical contact with conductor 22 when spring 28b is depressed. Holes 30 provide means to accommodate rivets that can hold together the two molded parts that make up the switch housing. Plungers 31a and 31b are used as means to depress the springs 28a and 28b.

Tabs 32 and 33 are used to position conductors 22 and 23 respectively and to prevent these conductors from moving axially within the switch housing. Terminals or tabs 34, 35 and 36 mate with commercially available spring receptacles that are joined electrically to conductors at their other end.

Cavity 37 accommodates a lamp 18, or a Fiber Optic bundle 19 in combination with an adapter that effectively increases the diameter of the bundle to fit snugly within lamp cavity 37.

Screw 38 retains the Fiber Optic bundle in place.

Figure 8:
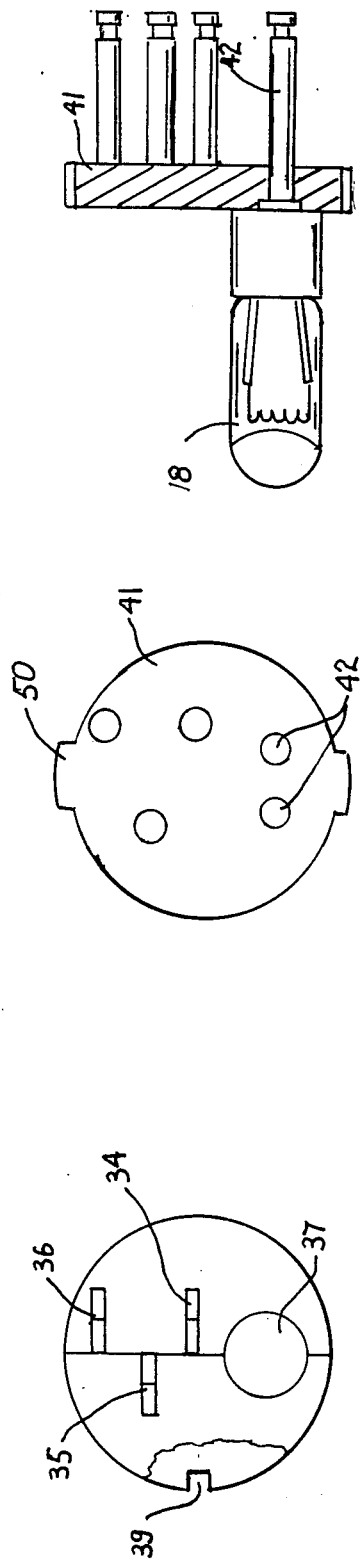
FIG. 8 is an enlarged end view, partially in section, of the switch assembly.

Channel 39 shown in FIG. 8 runs longitudinally along both sides of the switch housing, and mates with corresponding ribs 40 on the bore of handle 1.

When switch housing 17 is assembled into handle bore 3, the mating of aforedescribed ribs and channels aligns the switch housing and positions the plungers 31a and 31b so that they are directly in line with buttons 2a and 2b.

Figure 10:
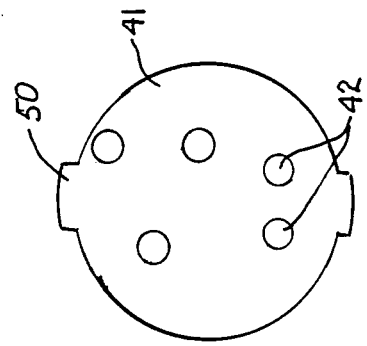
FIG. 10 is an enlarged side view, partially in section, of the lamp holder with assembled lamp.
Figure 9:
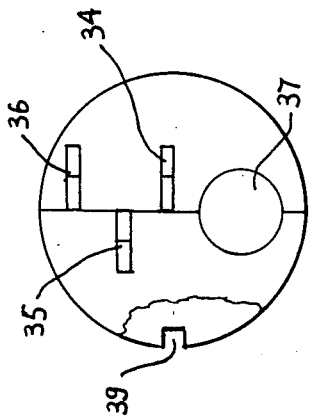
FIG. 9 is an enlarged end view of the lamp holder.

Lamp holder 41, shown in FIGS. 5, 9 and 10, incorporates commercially available spring receptacles 42 that accommodate tabs 34, 35, 36 and contact pins of lamp 18. The spring element of the receptacles provides electrical contact between tabs or pins to the receptacles. The receptacles, in turn, are electrically joined to electrical conductors.

End cap 10 is made of an electrically insulating material which is preferrably sterilizable, and upon assembly, exerts an axial force against the outer periphery of switch house 17, thereby containing, in a snug fashion, all the components within holder 1. The end cap 10 incorporates two slots 46 that are directly opposite each other. These slots are meant to accommodate the two ears 50 contained on the outer surface of lamp holder 41.

End cap 10 also incorporates an annular groove for accommodating a rubber o-ring 48. When the end cap is assembled into the handle, the o-ring becomes compressed and provides a radial seal against the inner diameter of the handle, thereby preventing water from entering the handle from its connecting ends. End cap 10 also incorporates a detenting pin 49 used to latch the end cap in place.

Cable assembly 43 is a 5 conductor cable, three conductors of which are soldered to the receptacles that mate with conductor tabs 34, 35 and 36, and two conductors of which are soldered to the two receptacles 42 which house the lamp pins.

The other end of the cable assembly branches into two cable sections, one comprising the three conductors that are electrically connected to conductors 22, 23 and 24. This branch terminates into a plug terminal 44 that mates with handswitch outlets of the current electrosurgical current generating unit.

The other branch of cable assembly 43 contains the two conductors that are electrically joined to the pins of the lamp at their opposite end. The two conductors in this leg are electrically attached to a power source such as a step down transformer, with or without a line switch, which provide current to the lamp. The two branches of the cable are separated and kept apart by shrink sleeve 45. The walls of this shrink sleeve are of a type that can adhere to each other at the acute angle formed by the two conductor branches of cable assembly 43.

In a typical sequence of assembly which uses an electrically operated lamp as the light transmitting means, end cap 10 is first slid back over cable assembly 43, and the five conductors exiting from the cable assembly 43 are electrically connected to receptacles 42.

Once this is done, the lamp holder 41 is then assembled to the end cap 10 by engaging its ears 50 into slots 46 in the end cap. Lamp 18 is then assembled to the lamp holder by engaging its pins into the appropriate spring receptacles 42.

Bushing 9 is then assembled into bore 6 of handle 1. To insure that the bushing stays in place, its surface, that locates again shoulder 7, can be treated with adhesive, such as epoxy so that it sticks to shoulder 7.

Once the bushing is in place, the switch housing 17 is inserted into main bore 3 of handle 1, making sure as it is inserted that its channels 39 mate with ribs 40 within bore 3. Once the switch housing is in place, the end cap is inserted into bore 3 in an orientation that will allow its assembled lamp to enter chamber 37 of the switch housing first, followed by the engagement of tabs 34, 35 and 36 into receptacles 42 assembled to lamp holder 41. The end cap continues to be inserted until its detenting pin 49 snaps into a mating hole or annular groove within the inner diameter of handle 1.

When electrode 11 is inserted into handle 1, it first enters bore 4, proceeds into bore 5, into the inner diameter of bushing 9, and finally into cavity 20 of the switch housing 17, proceeding until the electrode seats against shoulder 21 in switch housing 17. In the process, insulation 16 seats against shoulder 8 of bore 4, and an uninsulated portion of tubular element 13 makes electrical contact by means of spring element 25 with common conductor 24. Because the inner diameter of bushing 9 is smaller than the outer diameter of tubular element 13, it provides a water tight seal around electrode 11. When depressed, the outer diameter of the bushing will expand and provide a water tight seal along its outer periphery.

The final assembly procedure is to insert buttons 2a and 2b into appropriate holes in holder 1, thereby, depressing bushing 47 until the buttons snap into place.

Surface 49 of the buttons will retain the buttons in place while bushing 47 is under compression. This compressive action acts to provide a seal against liquid entry in the button area, and will also retain the buttons in a snug fashion.

Compression of button 2a will cause plunger 31a to depress the spring 28 that causes leaf 27 to snap into electrical contact with conductor 23, which in turn will cause cutting current to reach the electrode 11.

Likewise, compression of button 2b will cause plunger 31b to depress the spring 30 that causes leaf 29 to snap into electrical contact with conductor 22 causing coagulation current to reach electrode 11.

While in the foregoing specification an embodiment of the invention has been set forth in considerable detail for purposes of making an adequate disclosure thereof, it will be apparent to those skilled in the art that numerous changes may be made in such details without departing from the spirit and principles of the invention.

What is claimed is:

1. A hand held electrosurgical instrument with means for providing localized illumination to the working area, comprising:
   (a) a cable connecting means to electrically connect said instrument to hand control output terminals of electrosurgery generators,
   (b) a holder with finger actuated switching means for selectively producing current for cutting or current for coagulation from said electrosurgery generators to which it is electrically connected,
   (c) an elongated electrode with a longitudinal axis which is releasably attached within said holder, and which has attached thereto a light guide means extending along said longitudinal axis, said elongated electrode and said light guide means having a first terminus within the said holder, and a second terminus outside of said holder,
   (d) a mounting means within the holder for holding a light source in close proximity to said first terminus of said electrode, and said light guide,
   (e) switching means for providing illumination independently of the electrosurgery current, and
   (f) a light source means mounted within said mounting means and providing light into said light guiding means to shine light out of said terminus to illuminate said working area.

2. The hand held electrosurgical instrument of claim 1 wherein the light guide means attached to said electrode comprises one or more fibers capable of transmitting light.

3. The hand held electrosurgical instrument of claim 2 wherein said light source is a filament type lamp having a pair of electrical contacts for making electrical connections to power source connecting means.

4. The hand held electrosurgical instrument of claim 2 wherein said light source means can be either a filament lamp, or a light transmitting Fiber Optic cable either of which is capable of being held in place within the holder of the instrument in close proximity to the first terminus of the electrode.

5. A hand held electrosurgical instrument with means for providing illumination to the area of surgery, comprising:
   (a) an elongated electrically insulative handle having an electrical connection end, an electrode receiving end and a longitudinal bore therethrough,
   (b) a surgical electrode with a metallic tubular element containing one or more fibers capable of transmitting light therethrough, said electrode inserted into the said receiveing end of the handle,
   (c) a switch housing having:
      (1) two switches for selectively producing high frequency current for specific types of surgery,
      (2) a light cavity for accommodating a lamp, or a fiber optic bundle, (3) a lamp or fiber optic bundle mounted within said light cavity, to provide a light Source, (4) a cavity for accommodating and positioning the said electrode so that its terminus within the switch housing is colinear to and in close proximity with the said lamp or fiber optic bundle, (5) three current carrying conductors in which one acts as common, one acts as a carrier of cutting current, and one conductor acts as a carrier of coagulating current, (6) a metallic spring element that is in electrical contact with the said common conductor, and which comes into electric contact with the electrode as the electrode is inserted into the switch housing, (d) buttons for finger actuating the switches in the switch housing, (e) said light source is a filament type lamp having a pair of electrical contacts for making electrical connection to power source connecting means, (f) a cable of conductors that is electrically connected at said handle's electrical connection end to said current carrying conductors in said switch housing, and to said lamp's electrical contacts of the lamp within, the other ends of the conductors that are joined to the current carrying conductors of said switch housing are electrically connectable to output terminals of an electrosurgical generator, whereas the other ends of the conductors that are electrically joined to the electrical contacts of the lamps are electrically joined to an independent power source, (g) an end cap mounted to an end of said handle that keeps all the components in said handle in a snug manner, while preventing liquid entry into the main bore of said handle.

6. The electrosurgical instrument in claim 5 wherein said switch housing is made of high temperature thermoset material, which incoporates means for aligning its switches with corresponding buttons in the holder when the switch housing is assembled into the longitudinal bore of said holder.

7. The electrosurgical instrument in claim 5 wherein said electrode incorporates a retaining sleeve that mechanically retains said electrode and also acts as a gripping member to facilitate insertion and extraction of said electrode from said handle of said electrosurgical instrument.

8. The electrosurgical instrument in claim 5 wherein said switches within the switch housing are of a snap action variety.

9. The electrosurgical instrument in claim 5 wherein said switch housing and said housing are one and the same.

10. The electrosurgical instrument in claim 8, further including compressed washers thereby preventing liquid ingress into said electrode receiving end of said handle or into cavities accomodating said finger actuated buttons.

11. The electrosurgical instrument in claim 10, further including means for readily removing and replacing said lamp.

12. The electrosurgical instrument in claim 11, where the means for readily removing and replacing said lamp, is a cylindrically shaped cap that is releasably attached to said handle and which mounts lamp holder in addition to closing the connecting end of the handle in a manner which in conjuntion with a compresible ring prevents liquid ingress into the bore of the handle of its connecting means.

* * * * *